United States Patent
Warnock, Jr. et al.

(10) Patent No.: US 8,142,415 B2
(45) Date of Patent: Mar. 27, 2012

(54) BRAIDED CATHETER REINFORCEMENT LAYER HAVING SHORT AXIAL FILAMENT SEGMENTS

(75) Inventors: Kenneth Warnock, Jr., Manchester-by-the-Sea, MA (US); Peter Lunn, Beverly, MA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 153 days.

(21) Appl. No.: 12/108,784

(22) Filed: Apr. 24, 2008

(65) Prior Publication Data

US 2009/0270839 A1    Oct. 29, 2009

(51) Int. Cl.
*A61M 25/00* (2006.01)
(52) U.S. Cl. ........ 604/527; 604/524; 604/525; 604/526; 623/1.53
(58) Field of Classification Search .... 604/95.01–95.05, 604/527, 280–282, 170.1, 524, 170.01, 525–526; 623/1.53
See application file for complete search history.

(56) References Cited

U.S. PATENT DOCUMENTS

| 467,585 | A | | 1/1892 | Struss |
|---|---|---|---|---|
| 2,158,266 | A | | 9/1937 | Aldrich |
| 2,362,688 | A | | 6/1941 | Dunn |
| 2,354,212 | A | | 7/1944 | Jeckel |
| 2,494,389 | A | | 1/1950 | Jeckel |
| 2,856,934 | A | | 10/1958 | Petillo |
| 5,019,057 | A | * | 5/1991 | Truckai ............ 604/527 |
| 5,057,092 | A | * | 10/1991 | Webster, Jr. ........ 604/527 |
| 5,334,169 | A | | 8/1994 | Brown et al. |
| 5,538,513 | A | | 7/1996 | Okajima |
| 5,755,704 | A | | 5/1998 | Lunn |
| 5,776,115 | A | | 7/1998 | Antoshkiw et al. |
| 6,213,995 | B1 | * | 4/2001 | Steen et al. ........ 604/527 |
| 6,942,654 | B1 | | 9/2005 | Schaefer et al. |

FOREIGN PATENT DOCUMENTS

| JP | 03141958 A | 6/1991 |
|---|---|---|
| JP | 2631320 B2 | 7/1997 |

* cited by examiner

*Primary Examiner* — Bhisma Mehta
*Assistant Examiner* — Edelmira Bosques (57) ABSTRACT

A catheter includes an elongate member having a braided reinforcing layer. The reinforcing layer comprises a plurality of continuous filaments that transform from a braided configuration to short axially oriented segments in a least one location along the catheter. Also disclosed is a method of manufacturing a braided elongate member including providing a core, forming at least one braided portion with a plurality of filaments and forming at least one short axially oriented segment with at least a portion of the same plurality of filaments.

6 Claims, 7 Drawing Sheets

FIG. 1

(Prior Art)

BRAIDED CATHETER REINFORCEMENT LAYER HAVING SHORT AXIAL FILAMENT SEGMENTS

FIELD OF THE INVENTION

This invention relates generally to medical catheters, and more particularly to the design and fabrication of catheters having a braided reinforcement layer with variably positioned axial strands.

BACKGROUND

Cardiovascular disease, including atherosclerosis, is a leading cause of death in the U.S. A number of methods and devices for treating this disease in vessels of the heart and throughout the vasculature have been developed, including a broad array of catheters and minimally invasive methods for using them. Catheter-based delivery systems are routinely used to introduce stents and other medical devices into the cardiovascular system for both therapeutic and diagnostic purposes.

Typically, the catheter is inserted into the vascular system percutaneously through an artery, such as the femoral, jugular, or radial artery. The catheter is threaded through the vascular system until the distal end of the catheter is adjacent to the treatment site. The position of the catheter end may be determined by common visualization methods such as fluoroscopy or ultrasound. To reach treatment sites distant from the insertion site, guiding catheters are typically used to provide a tubular conduit, open at both ends, and through which smaller devices are passed. Guiding catheters have as large a through-lumen as possible, given the constraints of a nominal outer diameter, e.g. 6 French (2.00 mm) and a wall thickness sufficient to provide the required functional properties.

In order to perform well, a guiding catheter must have sufficient columnar strength and rigidity so that it can be pushed through the vasculature of the patient without bending back on itself or kinking. However, if it is too stiff, it may cause damage to blood vessel walls. At the same time, the catheter must be sufficiently flexible so that it can follow a winding, sometimes tortuous, path through the patient's vasculature. In order to balance the need for both flexibility and columnar strength, catheters are frequently constructed to have a relatively rigid proximal section and a more flexible distal section. Such a balanced combination also provides a catheter with good steerability, which is the ability to transmit substantially all rotational inputs from the proximal end to the distal end. Controlled rotation of the distal end of a catheter is useful for directing catheters that have pre-formed or curved distal ends.

Known catheter designs attempt to achieve this balance of physical properties by using support layers of braided filaments combined with elongate axially oriented filaments within the wall of the catheter. A braided support layer provides resistance to crushing, kinking or radial expansion from internal pressure, while adding substantial torsional stiffness, and may add bending stiffness to the catheter. Elongate axial filaments increase tensile modulus of the assembly and also provide bending stiffness to the catheter.

The braided material is positioned along at least a portion of the length of the catheter. The axial filaments are also positioned along the length of the catheter, running alongside or within the braided layer. One drawback to a catheter having both a braided layer and an axial layer is that the catheter may be too stiff to traverse the tortuous vascular pathways. Another drawback to having a catheter with a multi-layer support layer is the added cost. Yet another drawback of the multi-layer support is that the multiple layers may create undesirable additional thickness of the catheter wall, especially in those catheters having the multi-layer support disposed between an outer polymeric bonding layer and an inner polymeric (liner) layer.

Figure 1:
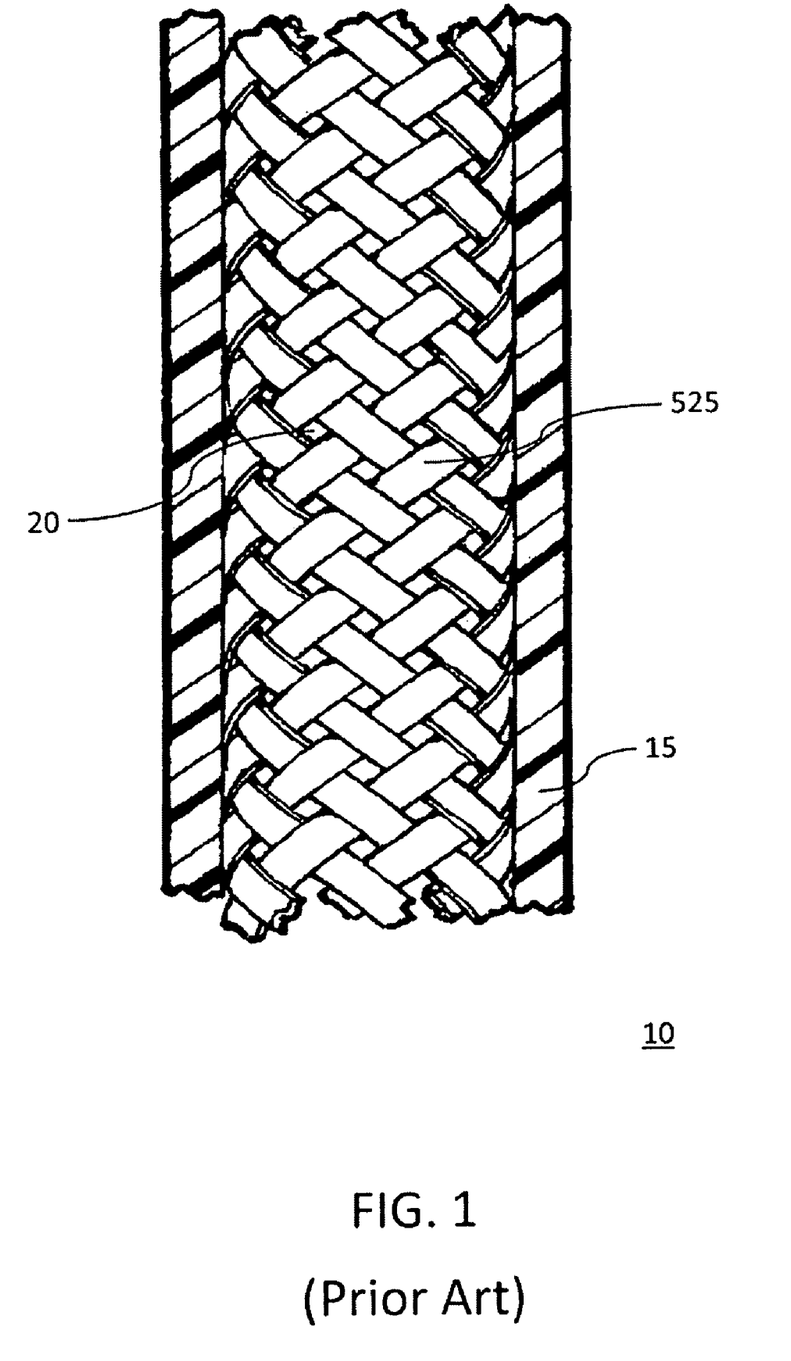
FIG. 1 illustrates a longitudinal cross section of a prior art vascular treatment device.

One solution to the undesirable increase in thickness of the catheter wall was to produce a liner-less catheter, such as catheter 10 illustrated in FIG. 1. FIG. 1 shows a longitudinal cross section of a portion of a liner-less catheter 10. Catheter 10 includes an outer polymeric layer 15 and a braided reinforcing (support) layer 20 composed of flat wire filaments 25. One drawback to a liner-less guiding catheter is that in use the treating clinician often feels a disconcerting "zipper effect" as a treating device is advanced through the catheter. This zipper effect is due to the device traversing the uneven inner surface of the support layer.

It would be desirable, therefore, to provide a catheter that has the advantages of both braided and axial support layers while overcoming these and other disadvantages.

SUMMARY OF THE INVENTION

One embodiment of the invention provides a catheter comprising an elongate catheter body having a reinforcing layer bonded to a polymeric bonding layer, wherein the reinforcing layer comprises a continuous plurality of filaments forming at least one braided portion and at least one short axial filament segment.

Another embodiment of the invention provides a method of manufacturing a braided elongate member. The method includes providing a core, attaching a plurality of filaments to a first end of the core and forming the plurality of filaments into a reinforcing layer surrounding the core, the reinforcing layer comprising at least one braided portion and at least one short axial filament segment, the at least one short axial filament segment transitioning from one of the plurality of filaments of the braided portion.

BRIEF DESCRIPTION OF THE DRAWINGS

The present invention is illustrated by the accompanying drawings of various embodiments and the detailed description given below. The drawings should not be taken to limit the invention to the specific embodiments but are for explanation and clarity. The detailed description and drawings are merely illustrative of the invention rather than limiting, the scope of the invention being defined by the appended claims and equivalents thereof. The foregoing aspects and other attendant advantages of the present invention will become more readily appreciated by the detailed description taken in conjunction with the accompanying drawings, which are not drawn to scale.

DETAILED DESCRIPTION

Throughout this specification, like reference numbers refer to like structures. Various types of catheters that incorporate the present invention include balloon catheters, infusion catheters, diagnostic catheters, drainage catheters, guiding catheters, introducer sheaths, laparoscopes, endoscopes and arthroscopes. The below description refers generally to a vascular treatment device though it is understood that many types of medical devices, including those listed above are encompassed by the present invention. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

Generally, as will be described below, the catheters of the present invention provide an elongated shaft having variable stiffness along the length of the shaft. The variable stiffness of the shaft is provided by a reinforcing layer that is composed of filaments that form both the braided portion and short axially oriented portions intermixed with the braided filaments. The braided portion has high torsional and columnar strengths sufficient to enable the vascular treatment device to be steered and pushed through a patient's vascular system or other body lumen without kinking. Exemplary embodiments of the braided elongate member and the manufacture of the braided elongated member are described below.

Figure 2:
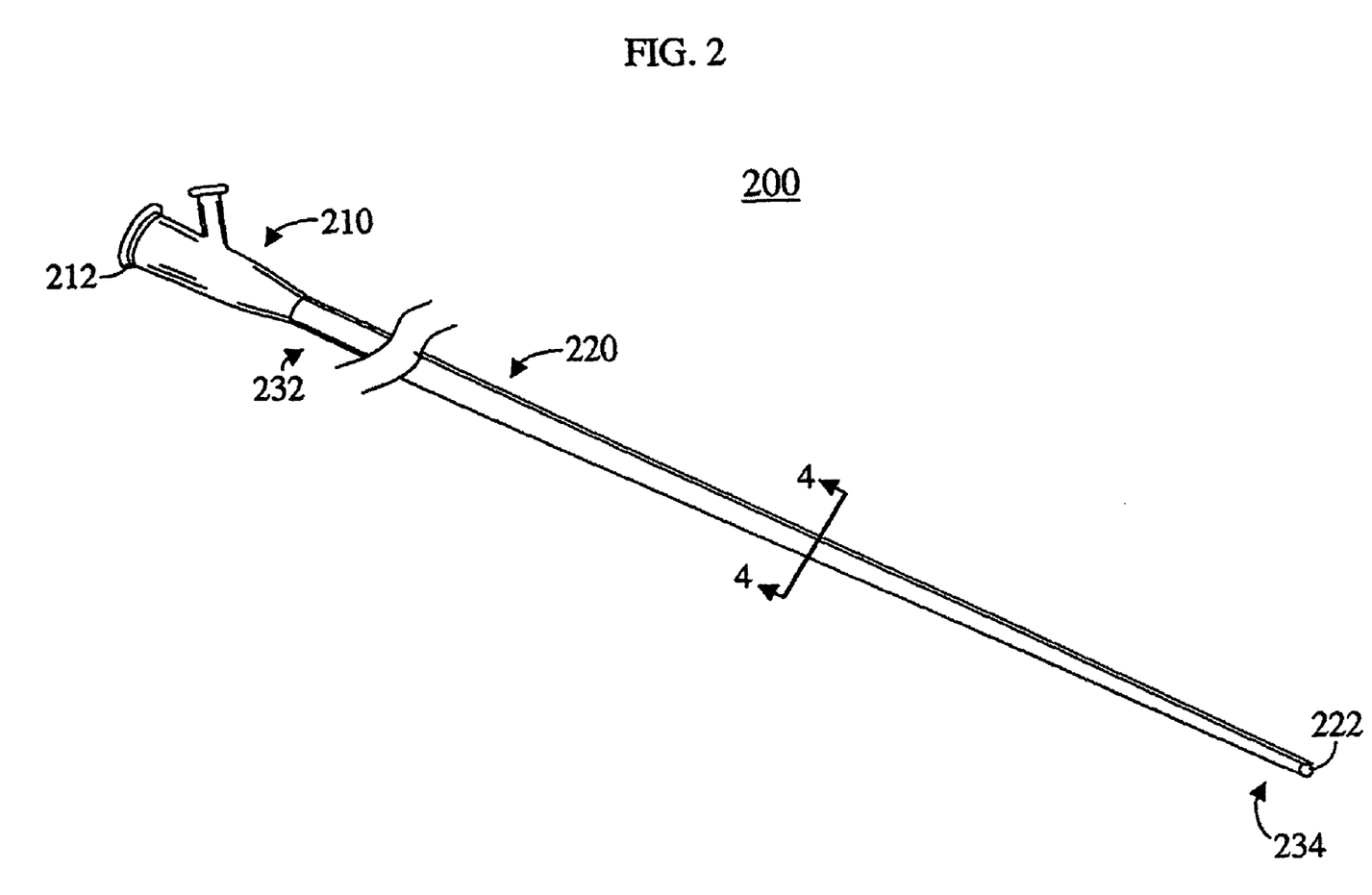
FIG. 2 illustrates one embodiment of a vascular treatment device having a braided and axial reinforcing layer made in accordance with the present invention.

FIG. 2 illustrates a vascular treatment device 200 made in accordance with the present invention. Vascular treatment device 200 includes proximal fitting 210 attached to a proximal end of catheter body 220. Proximal fitting 210 includes end port 212. Proximal fitting 210 may be any fitting suitable for providing port access to catheter body lumen 222 during treatment. Proximal fittings are well known in the art and will not be discussed further.

Figure 4:
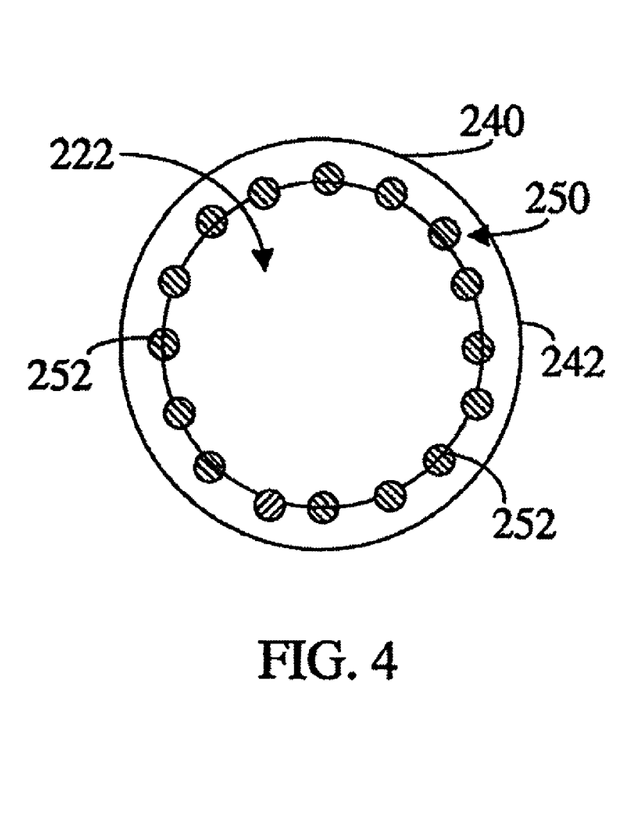
FIG. 4 shows a cross-section of the vascular treatment device of FIG. 2 taken along line 4-4.

Catheter body 220 has a proximal end 232 connected to proximal fitting 210 and a distal end 234. Referring now to FIG. 4, illustrated is a cross section of catheter body 220 taken along line 4-4 of FIG. 2. Catheter body 220 includes a catheter wall portion 240 defining lumen 222. Catheter wall portion 240 includes an outer polymeric bonding layer 242 and a reinforcing layer 250. Polymeric bonding layer 242 encases the reinforcing layer 250. Reinforcing layer 250 is composed of a plurality of filaments 252. The reinforcing layer 250 has a higher modulus of elasticity than the polymeric bonding layer that it is encased within. Polymeric bonding layer 242 may be manufactured from any suitable polymer or polymers such as, for example, polyamide, polyimide, polyolefins such as polyethylene or polypropylene, polyurethane, polyethylene block amide copolymer (PEBA), or fluoropolymers such as polytetrafluoroethylene (PTFE), fluorinated ethylene propylene (FEP), or perfluoroalkoxy (PFA). In one embodiment, polymeric bonding layer 242 is adhered to reinforcing layer 250 by adhesive.

Figure 6:
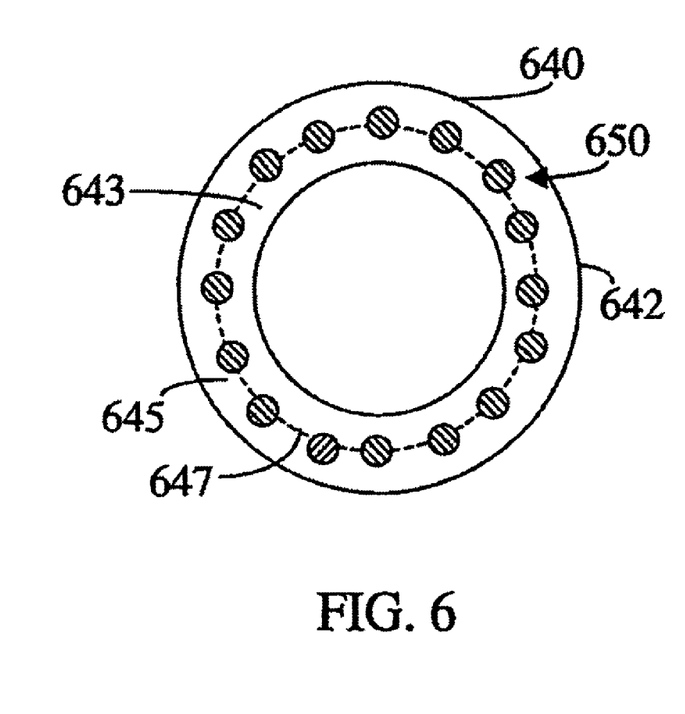
FIG. 6 shows a cross-section of another embodiment of a vascular treatment device in accordance with the present invention.

FIG. 6 illustrates a cross section of another embodiment of a catheter body having catheter wall portion 640 with a polymeric bonding layer 642. In this embodiment, polymeric bonding layer 642 is composed of two layers of polymeric material, a first (inner) layer 643 and a second (outer) layer 645. Inner layer 643 and outer layer 645 are fused together to encase reinforcing layer 650. The junction between inner layer 643 and outer layer 645 is delineated by dashed line 647. In one embodiment, inner layer 643 and outer layer 645 are adhesively or thermally bonded together around reinforcing layer 650 during the manufacturing process, as will be known to one of ordinary skill in the art of catheters.

Reinforcing layer 250, 650 is a braided and axial layer composed of a plurality of metallic or polymeric filaments 252. The filaments may be composed of any suitable biocompatible material such as, but not limited to, stainless steel, platinum, platinum alloy, titanium, titanium alloys, cobalt-chromium super alloy, nickel titanium (nitinol), tungsten or other medical grade metal, polyimide or other high-modulus medical grade polymer. Filaments 252 may include flat, oval or circular cross-sections. Filaments 252 used for reinforcing layer 250 typically have a diameter or thickness between 0.0005 inches and 0.0030 inches. The plurality of filaments 252 may combine individual filaments of different materials or cross-sectional shapes. Reinforcing layer 250 may span as much as the full length from catheter body proximal end 232 to catheter body distal end 234. The length of reinforcing layer 250 may be determined based on the particular application for the treatment device.

Figure 3:
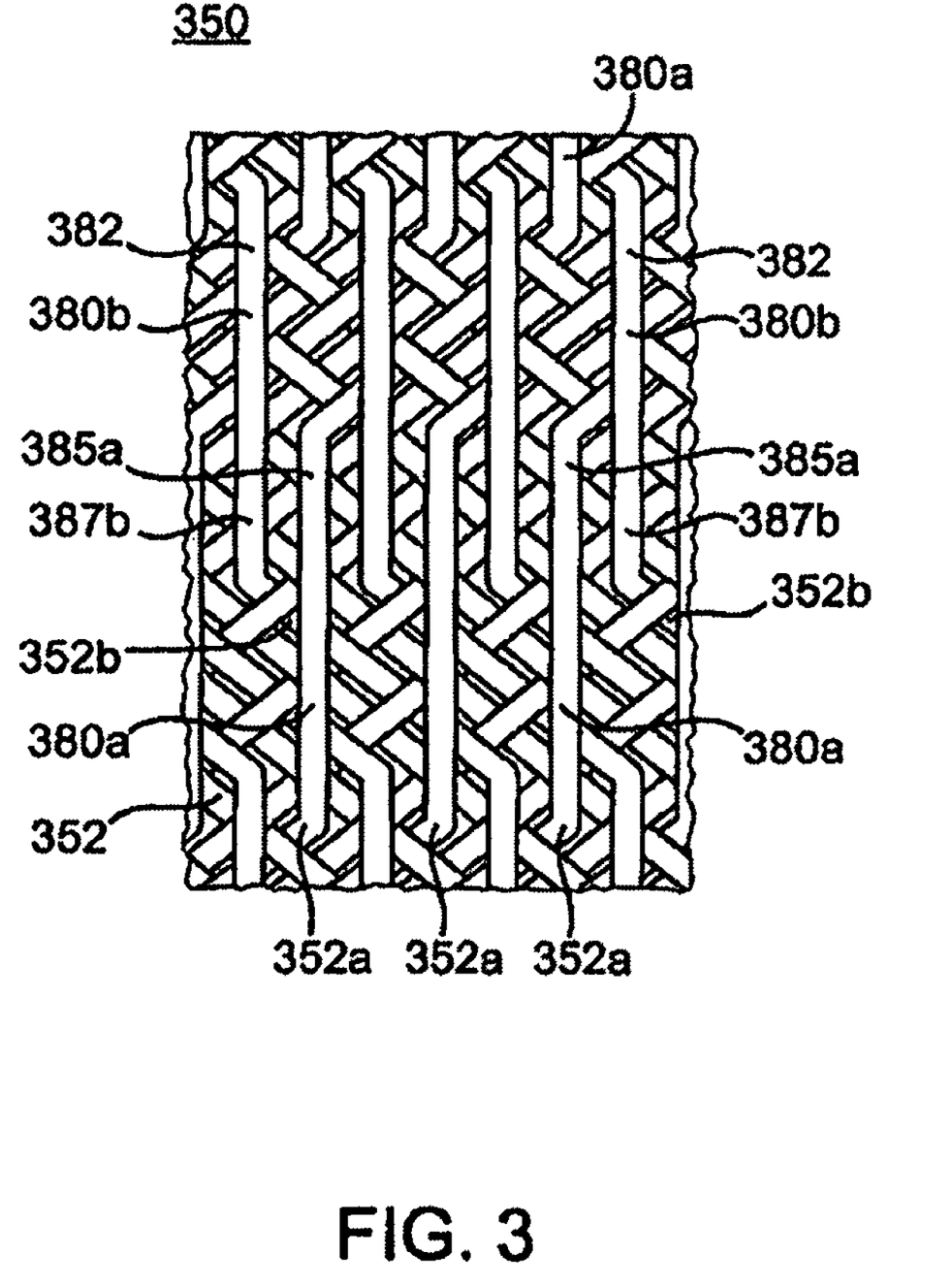
FIG. 3 illustrates a detailed view of a portion of a braided and axial reinforcing layer made in accordance with the present invention.

Filaments 252 form both the braided portions and the short axial filament segment portions of reinforcing layer 250, as best illustrated in FIG. 3. FIG. 3 illustrates a portion of reinforcing layer 350 made in accordance with the present invention. For purposes of illustration, layer 350 is shown as it would appear if the tubular braid layer 350 were cut open and laid flat, with no inner or outer polymer layers shown. To aid in the description, the distal direction, toward the distal end of the catheter, is upwards in FIG. 3. In an example, FIG. 3 illustrates a reinforcing layer composed of sixteen filaments 352 interwoven to form the braid. In a predetermined pattern, certain filaments that are forming braid 350 are isolated to form short axial filament segments 380. The short axial filament segments may be of various lengths and may be located to form various patterns depending on the application. For example, short axial filament segments may be located along the length of the catheter at a position where increased stiffness is required. In another embodiment, short axial filament segments 380 are disposed along the entire length of the catheter. In another embodiment, groups or bundles of short axial filament segments 380 are disposed in a staggered pattern along the entire length of the inner surface of the catheter. The filaments form a continuous cross-helical braid pattern.

Referring to FIG. 3, in one embodiment, a first portion of braiding filaments 352a exit from the cross-helical braid pattern to form short axial filament segments 380a, and then filaments 352a return to the cross-helical braid pattern. Similarly, a second portion of braiding filaments 352b exit from the cross-helical braid pattern to form short axial filament segments 380b, and then filaments 352b return to the cross-helical braid pattern. This pattern can continue along the entire length of the catheter body or for any other predetermined length. As illustrated in FIG. 3, the distal ends 385a of short axial filament segments 380a axially overlap proximal ends 387b of short axial filament segments 380b to form a staggered pattern of axial filament segments.

This pattern of braided and axial filaments is especially useful for liner-less catheters, such as that illustrated in FIGS. 2 and 4. In this embodiment, substantially parallel short axial filament segments are disposed among the braided filaments and exposed on an inner surface of the catheter to form an array of gliding segments along the entire length of the catheter, for example, gliding segments 382 shown in FIG. 3. In use, gliding segments 382 facilitate smooth axial movement of a treatment device through a liner-less guide catheter due to the staggered arrangement of the respective proximal and distal ends of adjacent short axial filament segments and by keeping the treatment device spaced away from the underlying filaments incorporated in the cross-helical braid pattern. Gliding segments 382 thereby reducing or eliminating the "zipper effect" of prior reinforcing layers of liner-less catheters such as the reinforcing layer illustrated in FIG. 1. The formation of braided and axial reinforcing layers 250, 350, 650 is discussed in more detail, below.

Figure 5A:
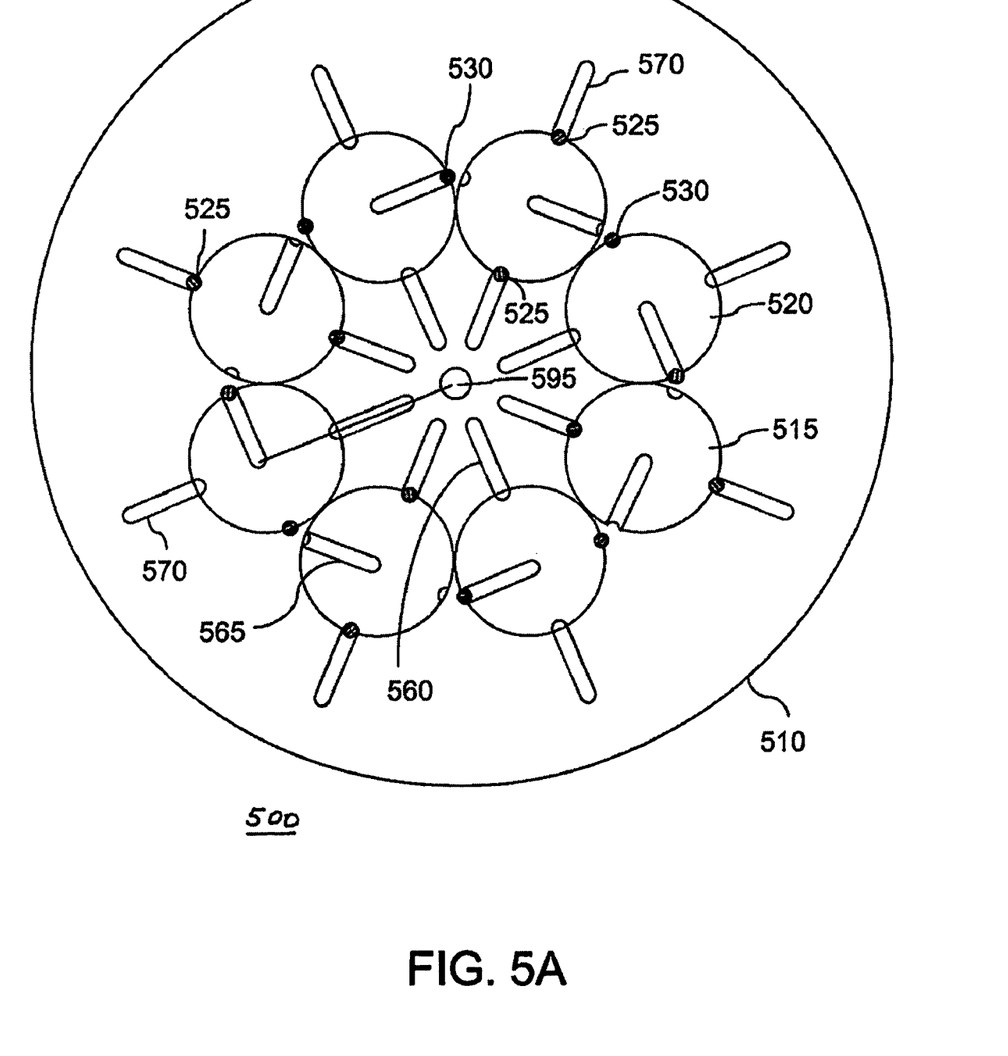
FIGS. 5A and 5B are schematic illustrations of one embodiment of a braiding machine in accordance with the present invention.
Figure 5B:
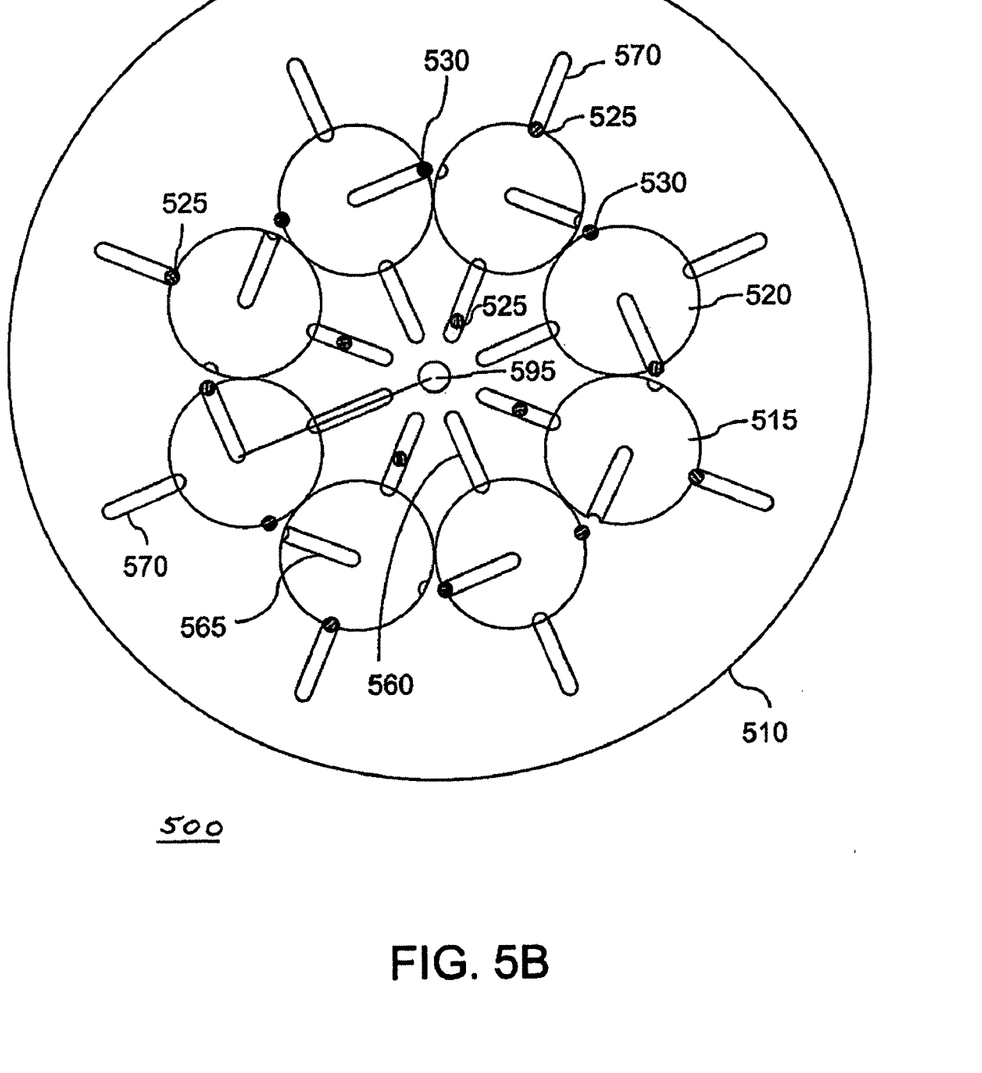

FIGS. 5A and 5B illustrate one embodiment of a braiding machine 500 for manufacturing catheter bodies reinforced with a filament layer having cross-helix braided segments and axial filament segments. Braiding machine 500 includes a braiding configuration and at least one axial configuration for forming the braided portion and the axial portion, respectively, of a reinforcing layer such as the reinforcing layers illustrated in FIG. 3.

FIGS. 5A and 5B illustrate top views of braiding machine 500. Braiding machine 500 is composed of a horizontal track plate 510, a gear train comprising a plurality of counter-rotating horn gears 515, 520, and a plurality of bobbin carriers 525, 530 arranged in a "Maypole" type of braiding configuration as is known in the art. Each bobbin carrier 525, 530 includes a removable spool or bobbin around which is wound a length of filament, for example filament 252. Track plate 510 includes sinusoidal tracks or grooves (not shown) that extend in a circular arrangement about the axis of the machine. The bobbin carriers 525, 530 are guided around the axis of the machine in these tracks. A first track moves bobbin carriers 525 in a clock-wise direction. A second track moves bobbin carriers 530 in a counter clock-wise direction. This movement of bobbin carriers 525 in a direction opposite of carriers 530 causes the carriers to pass inwardly and outwardly around each other to interlace the attached filaments. This interlacing of filaments forms the braided portion of the reinforcing layer.

Braiding machine 500 further includes a plurality of detour or divert paths 560, 565, 570 used in the formation of short axial filament segments. Bobbin carriers 525, 530 are moved from the braiding tracks to at least one of the divert paths 560, 565, 570 in the axial forming configuration. In one embodiment, each horn gear has three associated divert paths, inner divert path 560, middle divert path 565 and outer divert path 570. Filaments diverted from the braid formation to outer divert path 570 form axial filament segments located outside of the braid tube being formed. Filaments diverted from the braid formation to middle divert path 565 form axial filament segments located between the filaments, or within the wall thickness of the braid tube being formed. Filaments diverted from the braid formation to inner divert path 560 form axial filament segments located inside of the braid tube being formed such as, for example, gliding segments 382.

In one embodiment, braiding machine 500 includes an automatic switching mechanism for moving bobbin carriers 525, 530 from the sinusoidal braiding tracks to one of the divert paths, 560, 565, 570. In another embodiment, braiding machine 500 includes a gate to open the divert path 560, 565, 570 and an extract actuator to push bobbin carriers 525, 530 into the divert path 560, 565, 570 and an insert actuator to return bobbin carriers 525, 530 to the braiding track.

FIGS. 5A and 5B illustrates a braiding machine 500 with 8 horn gears 515, 520 and 16 bobbin carriers 525, 530, one bobbin carrier for each bobbin of filament used to form the braided portion of the reinforcing layer. Those with skill in the art will recognize that the reinforcing layer of a braided and axial catheter body may be formed from any number of filaments. For example, the braided portion of the reinforcing layer may be formed of 8 to 32 filaments. Catheters in accordance with the invention can also be manufactured with between 4 and 144 filaments. In some instances known as "double ended" or "tow" braiding configurations, the carriers may pay out multiple filaments, e.g. where two filaments are paid out from each bobbin. Those with skill in the art will also appreciate that the number of divert paths associated with each horn gear may vary from that which is illustrated and described. For example, in one embodiment, each horn gear has only an inner divert path associated with the sinusoidal pathway.

FIG. 5B illustrates the axial configuration of the braiding machine 500. As discussed above and described with reference to FIG. 3, filaments of the reinforcing layer transition from a braided portion to a short axial filament segment in a short transition region. The filaments transition from the cross-helical braided configuration to the short axial filament segments using a continuous filament by moving a bobbin carrier carrying the filament to be transitioned into one of the divert paths 560, 565, 570. Divert paths 560, 565, 570 provide a pathway that is used to temporarily move at least one bobbin carrier 525, for example, out of the sinusoidal track away from horn gears 515, 520, leaving the remaining bobbin carriers 525, 530 in place to continue to travel in a sinusoidal path around horn gears 515, 520. As illustrated in FIG. 5B, four bobbin carriers 525 are diverted to inner divert path 560 to allow the attached filament to pay out axially along the inside of the braid tube being formed before returning to the sinusoidal braid forming track.

In practice, braiding machine 500 can be used to manufacture one or a plurality of catheter bodies suitable for use in preparing a catheter. During manufacture, the free ends of the plurality of filaments 252 are attached to a core or mandrel 595 upon which the braided catheter body is formed. In one embodiment of the braiding machine made in accordance with the present invention, the reinforcing layer is formed directly on the outer surface of the core or mandrel 595. Removing the mandrel after applying an outer layer (see below) then exposes reinforcing filaments 252, 352 to the inner lumen 222 to form a liner-less, thin-walled catheter shaft (FIG. 4). In another embodiment, core 595 may include a layer of polymeric material removably disposed around core 595 to form an inner polymeric layer 643 of the catheter body (FIG. 6).

Core 595 is moved in an upward direction during manufacture of the braid. Those with skill in the art will understand that the pitch of the braid may be determined by how fast core 595 moves in the upward direction in relation to the rotation speed of horn gears 515, 520, which defines the speed at which the carriers revolve in their sinusoidal path around core 595. In one embodiment, the pitch of the braid is altered along the length of a catheter by adjusting the rate of speed at which core 595 is moving longitudinally relative to the rotation speed of horn gears 515, 520. In one embodiment known to those of ordinary skill in the art, filaments 252, 352 may be secured by pulling the over-braided catheter through a heated die to melt or soften inner polymeric layer 643 and to force the filaments to be embedded therein.

At predetermined positions and/or intervals, at least one bobbin carrier 525, 530 is removed from the sinusoidal path around core 595 to a divert path 560, 565, 570. The filament attached to bobbin carrier 525, 530 is allowed to pay out to form a short axial filament segment 380a, 380b. Once the predetermined length of the short axial filament segment is produced, bobbin carrier 525, 530 is moved back into re-engagement with the horn gears such that bobbin carriers 525, 530 can resume travel in a sinusoidal path around horn gears 515, 520 to begin forming another braided portion. FIG. 5B illustrates four bobbin carriers 525 being diverted into inner divert path 560. FIG. 3 illustrates reinforcing layers 350 composed of sixteen filaments. In these embodiments, two groups of four bobbin carriers were diverted in a staggered manner to form an array of substantially parallel, staggered, short axial filament segments 380a and 380b. Bobbin carriers having filaments are diverted to form short axial filament segments and returned to continue with forming the braid portion as required to produce the desired pattern of braided portions and intermixed short axial filament segments for the catheter body. The bobbin carrier may be diverted based on length of time, rate of movement of the core or any other measurement suitable to obtain short axial filament segments of the desired length. Those with skill in the art will appreciate that the length of the short axial filament segments can vary depending on such factors and placement of the short axial filament segments, length of catheter body and purpose of the short axial filament segment. As an exemplary range, short axial filament segments may be from 0.05 to 6.00 inches long. In one embodiment, short axial filament segments are 0.25 inches long.

Upon completion of the reinforcing layer having braided and short axial filament segments, an outer layer of polymeric material 245 is bonded to the outer surface of the reinforcement layer 250. The outer layer of polymeric material may be bonded to the reinforcement layer 250 by any suitable method such as by over-extrusion or adhesive bonding. In another embodiment, a heat shrink tube is placed around the outer polymeric layer and heated in such a manner and for a sufficient time to shrink the heat shrink tube, soften and compress the outer polymeric layer and form a thermal bond between the inner polymeric layer (if present) and the outer polymeric layer. The heat shrink tube is removed upon completion of the bonding process. Bonding the inner polymeric layer to the outer polymeric layer entraps the braided portions and axial filament segments of the reinforcing layer.

Finally, core 595 is removed and a fitting 210 is affixed to the proximal end of catheter body 220. Other finishing steps may also be performed on catheter body 220, such as adding a soft distal tip, heat-forming a desired curve shape or applying any of various coatings to the inner or outer surfaces of the catheter. Referring to FIG. 6, the addition and bonding of the outer layer 645 of polymeric material to the inner polymeric material 643 may occur any time after formation of the braid. For example, in one embodiment, as soon as the braid is formed on the core the outer layer of polymeric material 645 is formed over the inner layer by a solution coating process that applies, e.g., by dipping or spraying, an uncured liquid polymer around the filaments, subsequent to which the polymer can be cured by solvent evaporation, cross-linking, or other reaction. This process may continue until the reinforcing layer 650 is completely encased. In another embodiment where the braid is formed directly on the core or mandrel, the outer polymeric layer may be formed in a similar solution coating process.

Figure 7:
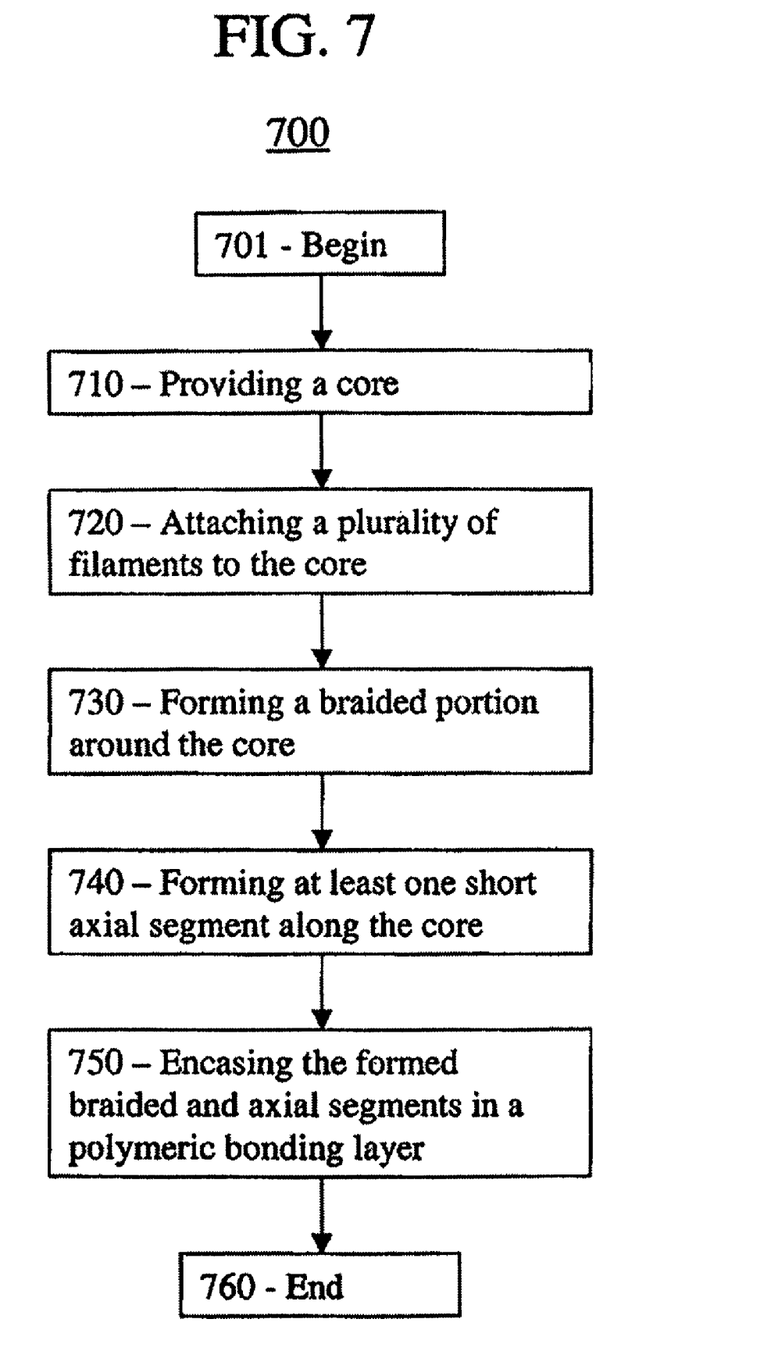
FIG. 7 is a flow chart of one embodiment of a method of manufacturing an elongate member having a braided portion and at least one short axial filament segment, in accordance with the present invention.

FIG. 7 illustrates a flow chart of one embodiment of a method of manufacturing a braided elongate member having at least one short axial filament segment. Method 700 may be performed on the braiding machine 500 described above and illustrated in FIGS. 5A and 5B.

Method 700 begins at 701. A core 595 is provided on a braiding machine 500 (Block 710). At least one braided catheter body with at least one short axial filament segment is formed on core 595. In one embodiment, a first polymeric layer 643 is removably mounted about the core 595 prior to forming the braided portions and short axial segments of the catheter body. In another embodiment, the braid is formed directly on core 595. A plurality of filaments 252, 352 is attached to a first end of the core (Block 720). Next, the plurality of filaments 252, 352 is formed into at least one braided portion 355 surrounding the core (Block 730). The braided portion may be formed by braiding machine 500. At least a portion of the plurality of filaments that form braided portion 355 is used to form at least one short axial filament segment 380a, 380b along the core (Block 740). As described in detail above, the at least one filament 352a, 352b from the plurality of filaments forming the braided portion transitions to the at least one short axial filament segment 380a, 380b. Next, the formed braided and axial reinforcing layer is encased in a polymeric bonding layer by bonding an outer polymeric layer 245 to the reinforcing layer and an inner polymeric layer, if present (Block 750). Method 700 ends at 760.

Formation of the braided and short axial filament segments for method 700 may be accomplished by any one or more of the processes described above and illustrated in FIGS. 5A to 5B. In one embodiment, the at least one braided portion is formed by moving a first plurality of bobbin carriers 525 in a clock-wise direction and moving a second plurality of bobbin carriers 530 in a counter clock-wise direction and the at least one short axial filament segment is formed by moving at least one bobbin carrier to an outer divert pathway 570.

In another embodiment, the at least one short axial filament segment portion is formed by moving one or more of the first plurality 525 or the second plurality 530 of bobbin carriers to a middle diverter 565 and moving the remaining of the first plurality or the second plurality of bobbin carriers in either a clock-wise or counter clock-wise direction. In this or a similar embodiment, the reinforcing layer having at least one short axial filament segment positioned within the braid (i.e. a middle axial filament segment) is used for the construction of electrophysiology catheters. In this embodiment, the short axial filament segments are shielded by the braided filaments.

In another embodiment, a portion of the reinforcing layer comprises only short axial filament segments. This portion of reinforcing layer is formed by moving all of the bobbin carriers from the braiding tracks to divert paths for a short distance or time and then redirecting the bobbin carriers back to the sinusoidal braiding track.

While the invention has been described with reference to particular embodiments, it will be understood by one skilled in the art that variations and modifications may be made in form and detail without departing from the spirit and scope of the invention.

What is claimed is:

1. An elongate guide catheter body having a lumen extending between open proximal and distal ends and a central axis extending therethrough, the catheter body comprising: an outer polymeric bonding layer; and a tubular braided reinforcing layer encased within the outer polymeric bonding layer and comprising a continuous plurality of filaments wherein:

a) the continuous plurality of filaments comprising a first portion of the filaments and a second portion of the filaments, wherein the first and second portions form a continuous cross-helix braid pattern; and b) the second portion of the continuous plurality of filaments forms a plurality of short axial segments substantially parallel to the central axis wherein each of the filaments of the second portion is helically interwoven with the first portion of filaments and repeatedly exits the cross-helix pattern, extends axially along an inner surface of the cross-helix pattern and returns into the cross-helix pattern, the plurality of short axial segments thus forming gliding segments exposed on an inner surface of the catheter body to facilitate smooth axial movement of a treatment device through the guide catheter body.

2. The elongate guide catheter body of claim 1 wherein a first plurality of short axial segments alternates and axially overlaps a second plurality of short axial segments along the entire length of the catheter body.

3. The elongate guide catheter body of claim 1 wherein the polymeric bonding layer is bonded to an outer surface of the reinforcing layer.

4. The elongate guide catheter body of claim 1 wherein the reinforcing layer comprises one or more materials selected from the group consisting of stainless steel, platinum, platinum alloy, titanium, titanium alloys, cobalt-chromium super alloy, nickel titanium (nitinol), tungsten, medical grade metal, polyimide and high-modulus medical grade polymer.

5. The elongate guide catheter body of claim 1 wherein the polymeric bonding layer comprises one or more materials selected from the group consisting of polyamide, polyimide, polyolefin, polyethylene, polypropylene, polyurethane, polyethylene block amide copolymer (PEBA), fluoropolymers, polytetrafluoroethylene (PTFE), fluorinated ethylene propylene (FEP), and perfluoroalkoxy (PFA).

6. The elongate guide catheter body of claim 1 wherein the plurality of filaments comprises between 8 and 32 filaments.

* * * * *